United States Patent
Dietz

(10) Patent No.: US 11,154,245 B2
(45) Date of Patent: Oct. 26, 2021

(54) VALIDATING CONTINUAL PROBE CONTACT WITH TISSUE DURING BIOELECTRIC TESTING

(71) Applicant: Vine Medical LLC, Saint George, UT (US)

(72) Inventor: Phillip W. Dietz, Saint George, UT (US)

(73) Assignee: Vine Medical LLC, Saint George, UT (US)

( * ) Notice: Subject to any disclaimer, the term of this patent is extended or adjusted under 35 U.S.C. 154(b) by 0 days.

(21) Appl. No.: 16/711,332

(22) Filed: Dec. 11, 2019

(65) Prior Publication Data

US 2020/0178896 A1 Jun. 11, 2020

Related U.S. Application Data

(60) Provisional application No. 62/778,076, filed on Dec. 11, 2018.

(51) Int. Cl.
*A61B 5/24* (2021.01)
*A61B 5/00* (2006.01)

(52) U.S. Cl.
CPC ............ *A61B 5/6843* (2013.01); *A61B 5/24* (2021.01); *A61B 2560/0418* (2013.01)

(58) Field of Classification Search
CPC .. A61B 5/6843; A61B 5/04; A61B 2560/0418
See application file for complete search history.

(56) References Cited

U.S. PATENT DOCUMENTS

| | | | | |
|---|---|---|---|---|
| 4,331,161 A * | 5/1982 | Patel | ............ | A61B 5/01 600/22 |
| 6,188,470 B1 * | 2/2001 | Grace | ............ | A61B 5/411 356/39 |
| 6,488,679 B1 * | 12/2002 | Swanson | ............ | A61B 18/1206 606/34 |
| 6,526,300 B1 * | 2/2003 | Kiani | ............ | A61B 5/14552 600/322 |
| 7,542,796 B2 * | 6/2009 | Horne | ............ | A61B 5/0531 600/547 |
| 8,808,178 B2 * | 8/2014 | Lane | ............ | G06F 9/453 600/300 |
| 2004/0087838 A1 * | 5/2004 | Galloway | ............ | A61B 5/7435 600/300 |

(Continued)

FOREIGN PATENT DOCUMENTS

WO 2018064471 A1 4/2018

*Primary Examiner* — Nay Tun
(74) *Attorney, Agent, or Firm* — Terrence J. Edwards; TechLaw Ventures, PLLC

(57) ABSTRACT

The disclosure extends to methods, systems, and computer program products for validating continual probe contact with tissue during bioelectric testing. The disclosure extends to methods, systems, devices, and computer program products that could be utilized to validate continual probe or probe hood contact with a test subject's tissue or tissue surrounding a test point. The methods, systems, and computer program products may be included with skin or tissue contact validation, warnings, alerts, and systems and procedures that could invalidate a compromised reading and initiate a new reading at the compromised test point.

20 Claims, 10 Drawing Sheets

(56) References Cited

U.S. PATENT DOCUMENTS

| | | | | |
|---|---|---|---|---|
| 2006/0064024 A1* | 3/2006 | Schnall | ............... | A61B 5/02007 |
| | | | | 600/500 |
| 2006/0184048 A1* | 8/2006 | Saadat | ................. | A61B 1/0008 |
| | | | | 600/478 |
| 2008/0033290 A1* | 2/2008 | Saadat | ............... | A61B 1/00096 |
| | | | | 600/433 |
| 2008/0267457 A1* | 10/2008 | Ali | ..................... | G06K 9/00053 |
| | | | | 382/115 |
| 2014/0012136 A1* | 1/2014 | Suzuki | ................. | A61B 5/0059 |
| | | | | 600/473 |
| 2015/0313488 A1* | 11/2015 | Dietz | ................... | A61B 5/0532 |
| | | | | 600/372 |
| 2016/0242672 A1* | 8/2016 | Mikoshiba | ......... | A61B 5/02416 |
| 2016/0331216 A1* | 11/2016 | Kaneko | .............. | A61B 1/00045 |
| 2017/0020411 A1* | 1/2017 | Gliner | .................. | A61B 5/0035 |
| 2018/0042557 A1* | 2/2018 | Park | ..................... | A61B 5/6828 |
| 2018/0314858 A1* | 11/2018 | Bertrand | ........... | H04W 12/0609 |

\* cited by examiner

500

Determining, Based On A Reading From The Contact Sensor, That The Probe Hood Is In Contact With The Body Tissue Of The Test Subject
502

Receiving A Biometric Measurement For The Test Subject From The Electrodermal Probe.
504

Determining, Based On The Reading From The Contact Sensor, Whether Contact Between The Probe Hood And The Body Tissue Is Broken.
506

Outputting An Alert In A Case Where It Is Determined That Contact Between The Probe Hood And The Body Tissue Has Been Broken
508

Invalidating The Biometric Measurement For The Test Subject From The Electrodermal Probe When It Is Determined That Contact Between The Probe Hood And The Body Tissue Has Been Broken
510

┌─────────────────────────────────────────────────────────────────────┐
│ Determining, Based On A Reading From The Contact Sensor, That The Probe Hood │
│ Is In Contact With The Body Tissue Of The Test Subject │
│ 802 │
└─────────────────────────────────────────────────────────────────────┘
                                    ↓
┌─────────────────────────────────────────────────────────────────────┐
│ Receiving A Biometric Measurement For The Test Subject From The Electrodermal │
│ Probe. │
│ 804 │
└─────────────────────────────────────────────────────────────────────┘
                                    ↓
┌─────────────────────────────────────────────────────────────────────┐
│ Comparing A Tip Force, Based On A Reading From The Tip Force Sensor, To A Hood │
│ Force, Based On A Reading From The Hood Force Sensor. │
│ 806 │
└─────────────────────────────────────────────────────────────────────┘
                                    ↓
┌─────────────────────────────────────────────────────────────────────┐
│ Determining, In A Case Where The Hood Force Is Less Than The Tip Force, That │
│ Contact Between The Probe Hood And The Body Tissue Is Broken. │
│ 808 │
└─────────────────────────────────────────────────────────────────────┘
                                    ↓
┌─────────────────────────────────────────────────────────────────────┐
│ Outputting An Alert In A Case Where It Is Determined That Contact Between The │
│ Probe Hood And The Body Tissue Has Been Broken │
│ 810 │
└─────────────────────────────────────────────────────────────────────┘
                                    ↓
┌─────────────────────────────────────────────────────────────────────┐
│ Outputting An Alert In A Case Where It Is Determined That Contact Between The │
│ Probe Hood And The Body Tissue Has Been Broken │
│ 812 │
└─────────────────────────────────────────────────────────────────────┘

FIG. 8

VALIDATING CONTINUAL PROBE CONTACT WITH TISSUE DURING BIOELECTRIC TESTING

CROSS-REFERENCE TO RELATED APPLICATIONS

This application claims the benefit of U.S. Provisional Application No. 62/778,076, filed Dec. 11, 2018, titled, "METHODS, SYSTEMS, AND DEVICES FOR VALIDATING CONTINUAL PROBE CONTACT WITH TISSUE DURING BIOELECTRIC TESTING," which is incorporated herein by reference in its entirety, including but not limited to those portions that specifically appear hereinafter, the incorporation by reference being made with the following exception: In the event that any portion of the above-referenced provisional application is inconsistent with this application, this application supersedes the above-referenced provisional application.

TECHNICAL FIELD

The disclosure is directed to obtaining bioelectric measurements using an electrodermal probe in contact with body tissue of a test subject, and is particularly directed to maintaining and verifying continual electrodermal probe contact with body tissue during bioelectric testing and/or measuring.

BACKGROUND

The electrical conductance of body tissue can be measured and analyzed to gather information about a body's condition and to aid in diagnosing certain conditions. One form of measuring electrical conductance of body tissue is Electroacupuncture According to Voll (EAV). EAV and other electrical conductance diagnostic systems measure conductance levels at meridian points of the body. These electrical conductance diagnostic systems are used by some health practitioners to gain additional insight into a test subject's body make up and condition.

EAV and other electrical conductance diagnostic systems often utilize an electrodermal probe in contact with the body tissue of a test subject in order to measure and/or test electrical conductance of the test subject's body tissue at meridian points of the body. These meridian points are located under the skin, which adds difficulty in measuring resistance.

In order to properly measure resistance/conductance of a test subject, a practitioner/technician may need to adjust the pressure of the electrodermal probe against the test subject's body tissue over the meridian point. Accordingly, taking a reading of a meridian point on a test subject's body may include locating the test point, placing a testing end of the electrodermal probe on the test point, and maintaining contact between the testing end of the electrodermal probe and the test subject's body tissue during testing/measuring while adjusting the pressure of the electrodermal probe against the test subject's body tissue. A practitioner/technician performing the measuring may need to adjust the force and rate of force of the testing end of the electrodermal probe against the point in a controlled manner.

However, it takes much time, training, and practice for a practitioner/technician to get to the point where he/she can take sufficiently accurate and repeatable meridian point readings. There are many things that the technician has to be aware of including controlling the proper rate of force and maintaining sufficient contact between the electrodermal probe and the body tissue. A typical technician can take six to twelve months, or more, of practice to become competent with electrical conductance diagnostic testing. Additionally, it may be difficult for an inexperienced technician to maintain sufficient continual contact between the electrodermal probe and the test subject's body tissue during bioelectric testing, or to know when contact between the electrodermal probe and the test subject's body tissue has been accidentally broken, thereby reducing reliability and accuracy of a reading.

In light of the foregoing, disclosed herein are systems, methods, and devices for achieving, detecting, and maintaining sufficient contact between a electrodermal probe and a test subject's body tissue during electrical conductance diagnostic testing.

BRIEF DESCRIPTION OF THE DRAWINGS

Non-limiting and non-exhaustive implementations of the disclosure are described with reference to the following figures, wherein like reference numerals refer to like parts throughout the various views unless otherwise specified. Advantages of the disclosure will become better understood with regard to the following description and accompanying drawings where:

FIG. 5 illustrates a schematic flow chart diagram of a method for validating contact between an electrodermal probe and a test subject;

FIG. 8 illustrates a schematic flow chart diagram of a method for validating contact between an electrodermal probe and a test subject;

DETAILED DESCRIPTION

Figure 1:
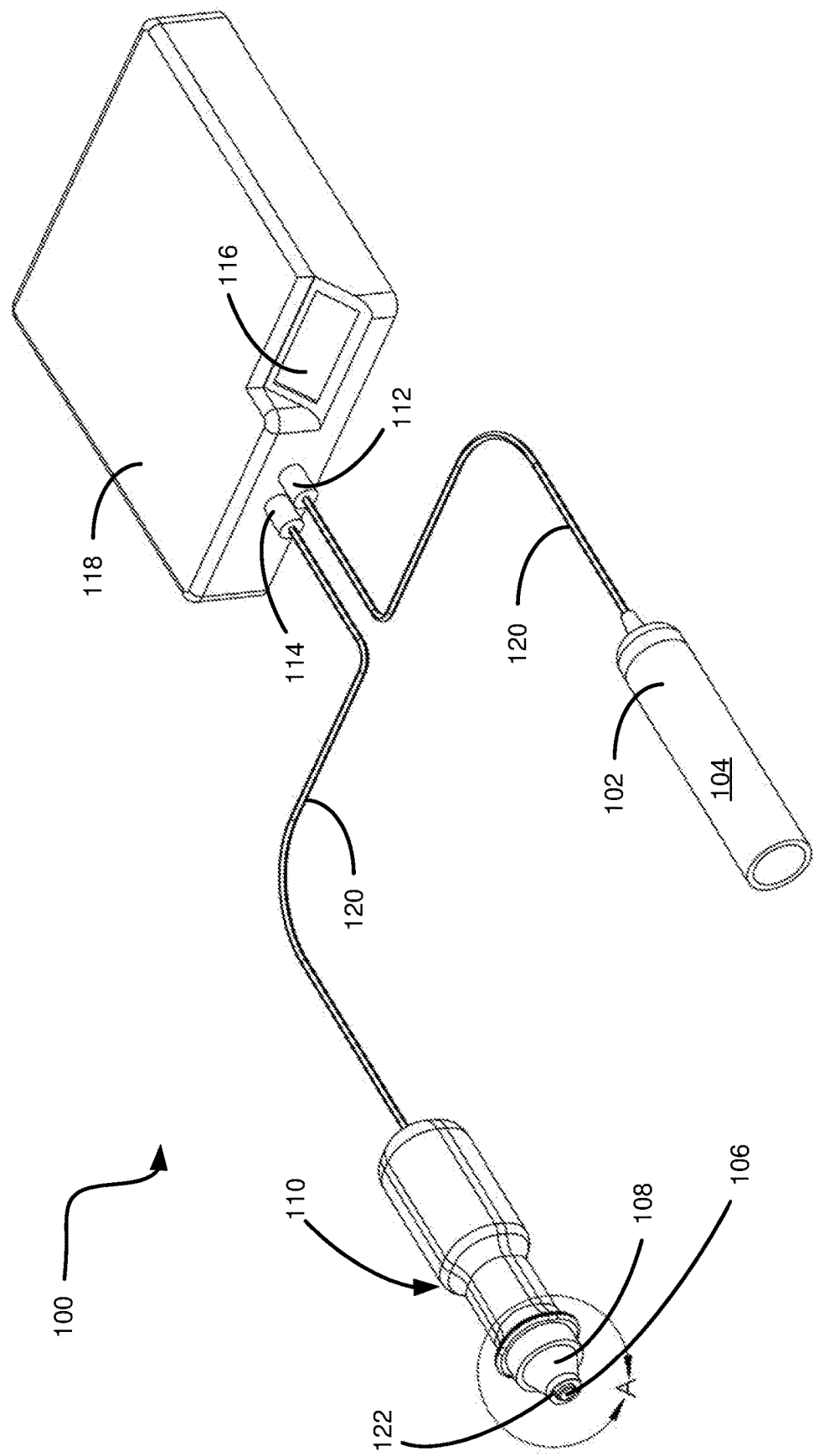
FIG. 1 illustrates an example system for obtaining bioelectrical measurements with a digital signal, including an electrodermal probe, a hand mass, and a bioelectrical measurement system and device.

Disclosed herein are systems, methods, devices, and computer program products for achieving, detecting, maintaining, and validating sufficient continual probe contact between an electrodermal probe and a test subject's body tissue during electrical conductance diagnostic testing. The disclosure extends to systems, methods, devices, and computer program products that could be utilized to validate continual contact between the testing end of the electrodermal probe and a test subject's body tissue or tissue surrounding a test point. The systems, methods, devices, and computer program products may be included with skin or tissue contact validation, warnings, alerts, and systems and procedures that could invalidate a compromised reading and initiate a new reading at the compromised test point. The systems, methods, devices, and computer program products may be used in conjunction with an electrical conductance diagnostic system such as an Electroacupuncture According to Voll (EAV) or other electrodermal sensor system.

An embodiment of the disclosure is a system for sensing the electrical conductance of a material such as body tissue. The system may sense the bio-conductivity of body tissue such as skin or some other tissue. As will be described in further detail below, an embodiment of the system includes an electrodermal probe for contacting a test subjects's skin and reading the electrical conductance of the test subjects's skin. The electrodermal probe may include a testing end that may include a tip positioned on the electrodermal probe to contact a site of the test subjects's skin and a probe hood that surrounds the tip of the electrodermal probe.

The measurements taken by the system can be assessed for determining a skin resistance measurement and/or a meridian conductivity measurement for the test subject. The meridian conductivity measurement may include a meridian stress assessment for measuring energy associated with acupuncture meridians. The measurements can be used in multiple healthcare practices such as bio resonance therapy, bio-energy regulatory techniques, biocybernetics medicine, computerized electrodermal screening, computerized electrodermal stress analysis, electrodermal testing, limbic stress assessment, meridian energy analysis, point testing, and others.

However, the measurements taken by the electrodermal probe can be inaccurate and ineffective if contact between the electrodermal probe and the test subject's body tissue or skin is unintentionally broken, which may lead to problematic and incorrect readings. It may be difficult for technicians using the electrodermal probe to know when contact between the electrodermal probe and the test subjects's body tissue or skin is broken, particularly if the technician is new or inexperienced in using electrodermal probes to obtain bioelectric conductance measurements. In light of this deficiency, disclosed herein are systems, methods, devices, and computer program products for achieving, detecting, and maintaining sufficient contact between a electrodermal probe and a test subject's body tissue or skin.

In the following description of the disclosure, reference is made to the accompanying drawings, which form a part hereof, and in which is shown by way of illustration specific implementations in which the disclosure may be practiced. It is understood that other implementations may be utilized, and structural changes may be made without departing from the scope of the disclosure.

Electroacupuncture According to Voll (EAV) devices can be deployed to measure conductance levels at meridian points in a body. An EAV device is a sensitive ohm meter for measuring resistance in the body. The resistance of a material, tissue, meridian pathway, and so forth can be assessed to calculate the conductivity of the material, tissue, and/or meridian pathway. A material with a lower resistance measurement will have a higher conductivity.

To detect resistance, an ohm meter (such as an EAV device) applies a small direct current flow through a material. Resistance measures the relative difficulty for current to flow through the material. Electrical conductors allow current to flow easily and have a correspondingly low resistance. Electrical insulators restrict current flow through and have a correspondingly high resistance. Ohm's Law applies to materials with a proportional relationship between voltage, current, and resistance according to:

$$V=RI$$

where V is voltage (measured in volts), I is current (measured in amps) and R is resistance (measured in ohms). Conductivity is the reciprocal of resistivity, expressed mathematically as 1/R and indicates a degree to which a specified material conducts electricity.

Human tissue generally has a resistance of about 98,000 Ohms between the tissue and ground. Meridian points have a general resistance of about 5,000 Ohms between the meridian point and ground. This means that meridian points throughout the human body are about twenty times more conductive than the tissue surrounding the points. This large differential in conductivity makes it possible to locate meridian points and to be very consistent in verifying the meridian points with an EAV device.

Now referring to the figures, FIG. 1 illustrates a perspective view of a bioelectric measurement system 100. As shown, bioelectric measurement system includes an electrodermal probe 110, grounding device 102, and a bioelectric measurement analyzing device 118 in electrical communication with electrodermal probe 110 and grounding device 102.

Grounding device 102 may include a handheld mass to be held by a test subject undergoing measurements by bioelectric measurement system 100. Grounding device 102 may include a rod made of brass, or any other suitable material for grounding the test subject. Grounding device 102 may include a grounding surface 104 disposed around an exterior of grounding device 102.

Grounding device 102 may be a small electrode similar to those used in conjunction with an electrocardiogram (EKG). Grounding device 102 may be any suitable size or shape and may be formed in an ergonomic size and shape that is easy fora test subject to hold in a palm of the test subject's hand. Grounding surface 104 may be of a sufficiently large size to provide ample grounding to take sufficiently consistent and sufficiently accurate measurements from the test subject.

Electrodermal probe 110 is configured to measure the resistance of skin, a meridian pathway in a body, or other materials or tissues. The readings taken by electrodermal probe 110 can be assessed to calculate the conductivity of the skin, the meridian pathway in the body, or other materials or tissues in the body. Electrodermal probe 110 may include a testing end, which may include a probe hood 108 and a probe tip 106 disposed at a distal end, or in other words testing end, of electrodermal probe 110 with respect to the electrical connection with bioelectric measurement analyzing device 118. Probe tip 106 may be placed against the skin of a test subject to enable electrodermal probe 110 to measure the resistance of the skin or meridian pathway in the test subject. In an embodiment, electrodermal probe 110 may take a measurement when probe tip 106 is pressed against tissue. Probe tip 106 may be constructed of any suitably electrically conductive material such as copper, silver, gold, aluminum, zinc, nickel, brass, iron, steel, or other material known to those skilled in the art.

In an embodiment, probe tip 106 is a single probe tip. In an alternative embodiment, probe tip 106 includes a plurality of individual probe tips. Probe tip 106 may be textured to help penetrate and help electricity flow through the insulation layer or cornified layer of the epithelial tissue without puncturing it. In another embodiment, grounding pads and/or contacts may be integrated with probe hood 108. Electrodermal probe 110 may further include a contact sensor 122 disposed on probe hood 108. Contact sensor 122 will be discussed in further detail below in connection with FIG. 3.

The bioelectric measurement analyzing device 118 may include one or more processors configurable to execute instructions stored in non-transitory computer readable storage media. Bioelectric measurement system 100 may include memory stored locally therein and accessible by bioelectric measurement analyzing device 118. Bioelectric measurement analyzing device 118 is in electrical communication with electrodermal probe 110, grounding device 102, and a display 116. In the illustration shown in FIG. 1, bioelectric measurement analyzing device 118 is in electrical communication with electrodermal probe 110 by way of a sensor connection point 114 and is in electrical communication with grounding device 102 by way of grounding connection point 112. The electrical communication between bioelectric measurement analyzing device 118 and electrodermal probe 110 and/or grounding device 102 can be facilitated by electrically conductive cables 120. Alternatively, the electrical communication may be made wirelessly through a wireless network such as a wireless personal area network (WPAN), a wireless local area network (WLAN), and so forth. Electrically conductive cable 120 may further be connected to a power source such that electrodermal probe 110 and/or grounding device 102 are powered by way of an external power source.

Figure 2:
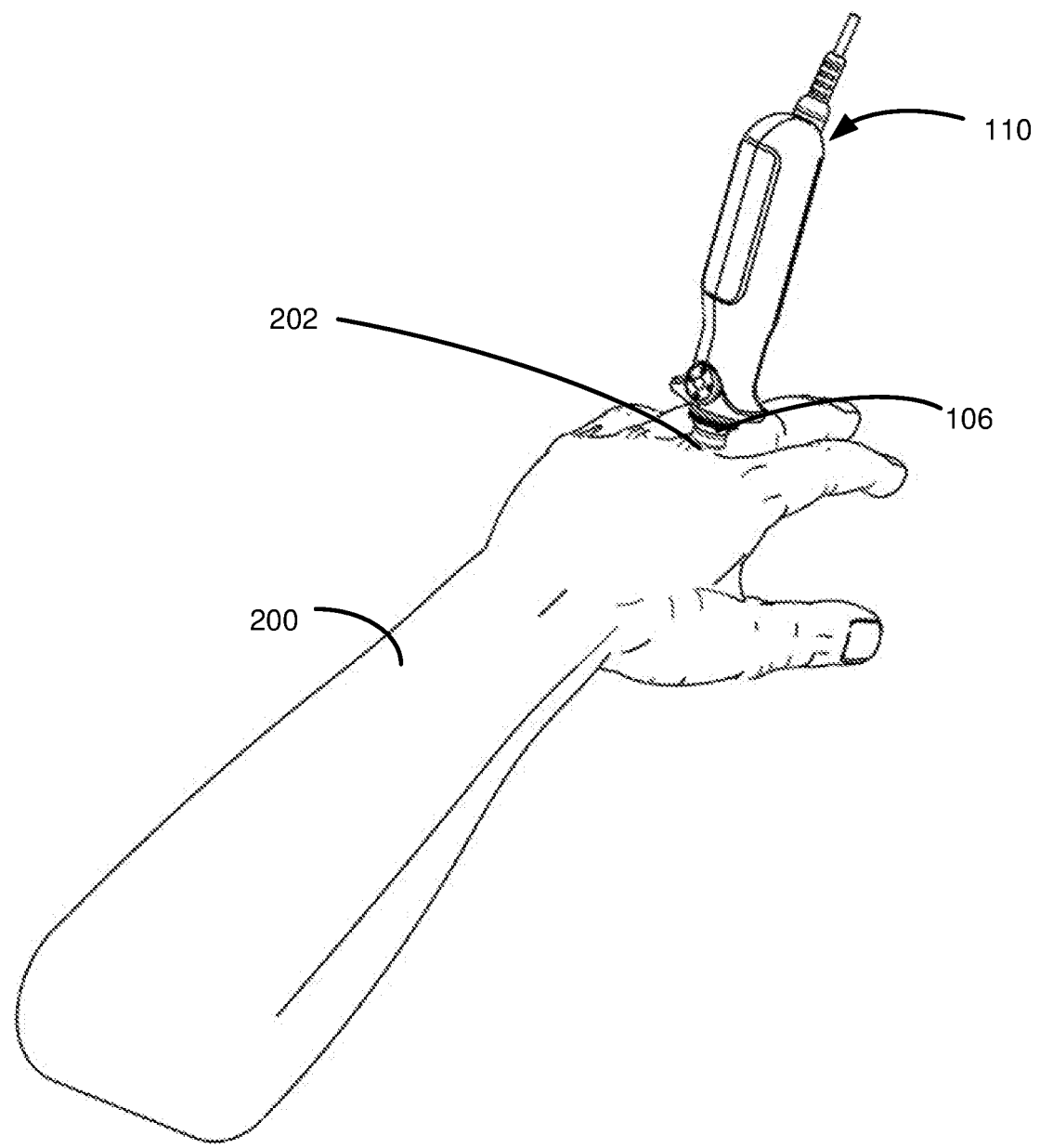
FIG. 2 illustrates an example electrodermal probe for obtaining bioelectrical measurements with a digital signal performing a bioelectric test at a skin site of a test subject.

According to one embodiment, conductance testing or measuring of meridian points may be done by having a test subject grip a conductive rod or hand mass (grounding device 102) in one hand while point readings are taken on the other hand and or the other side of the body using electrodermal probe 110. Then the conductive rod (grounding device 102) may be placed in the other hand while the point readings are taken on the other side of the test subject's body with electrodermal probe 110. Electrodermal probe 110 may utilize probe tip 106 to make contact with the meridian points, and the readings may be taken and recorded while pressure is applied against the tissue at that point. As illustrated in FIG. 2, the testing end of electrodermal probe 110, including probe tip 106, may be pressed against body tissue or skin of test subject 200 at a test point 202. It is understood that test point 202 shown on test subject 200 in FIG. 2 is exemplary and not limiting. Test point 202 may be found anywhere else on test subject 200 or any other test subject which may be subjected to such testing, not just at the location shown in FIG. 2.

A sequence in taking a meridian point reading from test subject 200 may be to first ground the test subject using grounding device 102 and then locate test point 202 and place probe tip 106 of electrodermal probe 110, on that test point 202. The technician may then adjust the force and rate of force applied on probe tip 106 against test point 202 in a controlled manner in order to obtain sufficiently accurate and reliable measurements. This sequence can take about 5 seconds and sometimes up to 20 seconds.

Meridian points are located under the skin which adds to the difficulty in measuring resistance because skin can become dry and act as an insulator. To minimize this insulator effect, several methods may be utilized, either alone or in combination. One method may include spraying a mist of water or other conductive liquid on the hand that grips grounding device 102 to help increase the conductivity of the tissue that is gripping grounding device 102. Grounding device 102 is the ground or reference in the test circuit. Another method is to add moisture or water to the tissue where the reading is taking place with electrodermal probe 110. Another method is to have a texture applied to the tip surface of probe tip 106 that helps penetrate the outer insulation layer of the skin or cornified layer of the epithelial tissue without puncturing it.

Another method to decrease the insulator effect of the skin is to adjust the pressure of probe tip 106 of electrodermal probe 110 against the test subject's body tissue over the meridian point. Accordingly, taking a meridian point reading of a meridian point on a test subject's body may include locating test point 202, placing electrodermal probe 110 on test point 202, and maintaining contact between probe tip 106 of electrodermal probe 110 and the test subject's body tissue during testing/measuring while adjusting pressure of probe tip 106 of electrodermal probe 110 against the test subject's body tissue. A practitioner/technician performing the measuring may adjust the force and rate of force of the tip of the electrodermal probe 110 against the point in a controlled manner in order to obtain sufficiently accurate and reliable measurements.

However, as discussed previously, it takes much time, training, and practice for a practitioner/technician to get to the point where he/she can take sufficiently accurate and repeatable meridian point readings. There are many things that the technician has to be aware of including the conductivity of the skin being tested, controlling the proper rate of force, recognizing and acquiring the proper aspects of a curve and slope of the reading, locating the proper point locations, maintaining contact between the tip and the body tissue, and the angle of the tip. A typical technician can take six to twelve months, or more, of practice to become competent with electrical conductance diagnostic testing. Additionally, it may be difficult for an inexperienced technician to maintain sufficient continual contact between the electrodermal probe and the test subject's body tissue during bioelectric testing or to know when contact between the electrodermal probe and the test subject's body tissue has been accidentally broken, thereby reducing reliability and accuracy of a reading.

This disclosure describes several systems, methods, devices, and computer program products to minimize the training time and improve accuracy and repeatability in meridian point readings and to ensure that sufficient contact between electrodermal probe 110 and test subject 200 is maintained. For example, in at least one embodiment electrodermal probe 110 may be an automated electrodermal probe that utilizes sensors, linear motors, and/or computerized controllers to properly control the force and rate of force probe tip 106 applies to test point 202 on test subject 200. In such a configuration, the force and rate of force probe tip 106 applies to test point 202 would be automated and controlled by a computerized system instead of the practitioner, thereby removing human error from testing and ensuring that proper contact and force is maintained between probe tip 106 of electrodermal probe 110 and test subject 200.

Such a configuration allows a beginning practitioner to take sufficiently accurate and repeatable readings just as a practitioner who has acquired the skill after years of practice. The configuration further allows even a beginning practitioner to maintain sufficient contact between probe tip 106 of electrodermal probe 110 and body tissue of test subject 200. Sufficiently accurate readings are possible as long as probe tip 106 is on the correct desired test location and at the correct angle and maintains or remains in constant sufficient contact with the tissue surrounding the test point.

Figure 3:
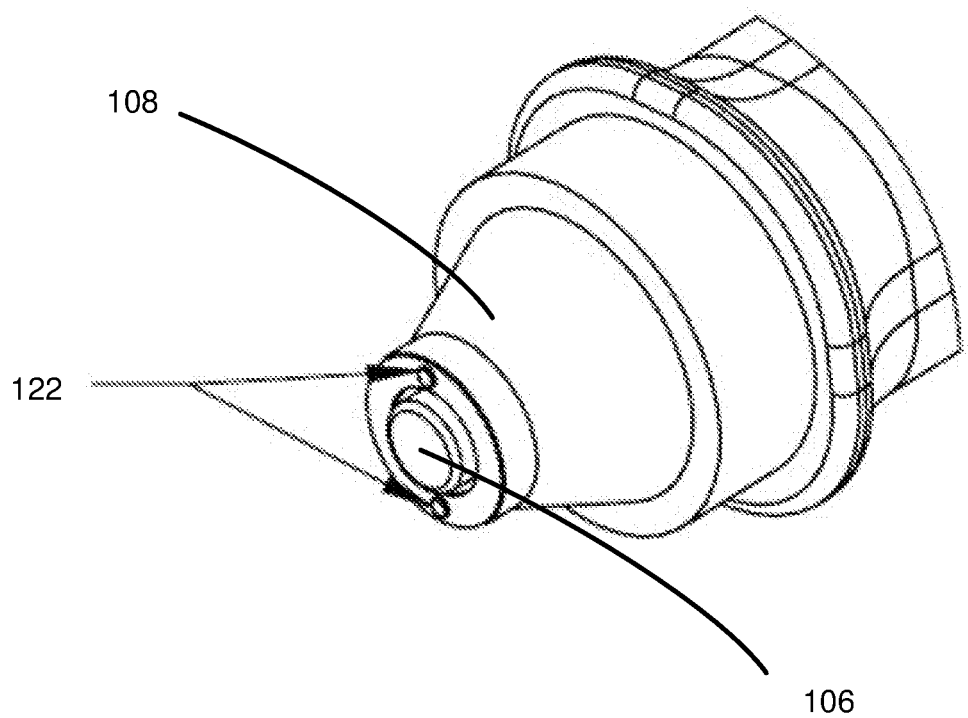
FIG. 3 illustrates a close-up detail view of a testing end of the electrodermal probe.

As illustrated in FIG. 3, testing end of electrodermal probe 110 may include probe hood 108 that surrounds and isolates probe tip 106 and test point 202 from unwanted practitioner inputs, which may result from practitioner interference with probe tip 106 and/or test point 202, and other outside inputs. FIG. 3 is a detail view of a testing end portion of electrodermal probe 110, specifically the portion of electrodermal probe 110 that is surrounded by circle A in FIG. 1. In such a configuration where electrodermal probe 110 includes probe hood 108, the practitioner may be able to individually control the force applied to test subject 200 by probe hood 108 independent of the force applied to test subject 200 by probe tip 106.

As further shown in FIG. 3, probe hood 108 may further include contact sensor 122 which determines whether contact is made between probe hood 108 and body tissue of test subject 200 surrounding test point 202. While FIG. 3 illustrates two contact points for contact sensor 122, the disclosure is not limited to only two contact points. Probe hood 108 may include one or more contact points for contact sensor 122.

Figure 4:
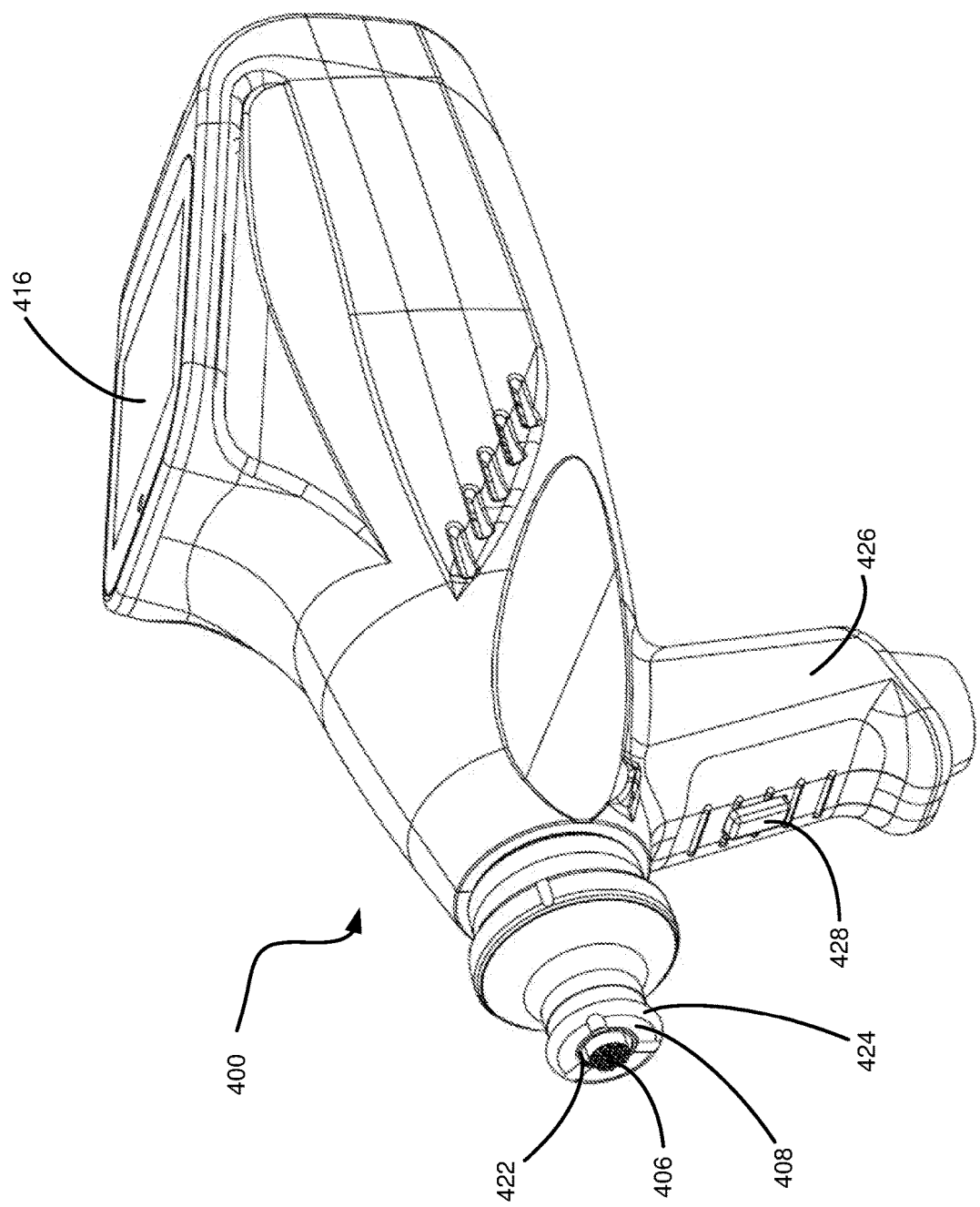
FIG. 4 illustrates an example electrodermal probe for obtaining bioelectrical measurements with a digital signal.

FIG. 4 illustrates various alternate configurations for an additional embodiment of an electrodermal probe. As shown in FIG. 4, electrodermal probe 400 may include a textured probe tip 406 that is textured to help penetrate and help electricity flow through the insulation layer or cornified layer of the epithelial tissue without puncturing it. Such a configuration allows the insulator effect of skin to be more efficiently overcome. The texture that may be applied to electrodermal probe 400 is not limited by this disclosure. Any texture, such as bumps, ridges, or waves, etc. may be applied to probe tip 406.

As further shown in FIG. 4, probe hood 408 may include contact sensor 422, which is in a shape of a conductive ring surrounding textured probe tip 406. Furthermore, grip pad 424 may be disposed around probe hood 408 to add comfort for a test subject being tested with electrodermal probe 400 and to add grip to prevent movement or slippage of electrodermal probe 400 while electrodermal probe 400 is in contact with a test subject. Grip pad 424 may be of any suitable size, shape (e.g., circular, ring-shaped, square, etc.), or material (e.g., rubber, foam, polymer, etc.) for accomplishing its purpose. Electrodermal probe 400 may further include a hand grip 426 to be held by a technician/practitioner during testing to provide convenience, comfort, and stability. Hand grip 426 may include trigger 428 which may be used to commence an operation of electrodermal probe 400, such as, for example, commencing/terminating testing on a test subject, or any other foreseeable operation. Electrodermal probe 400 may further include a display 416 for displaying readings, results, analysis, and/or other information to a practitioner, technician, and/or test subject of electrodermal probe 400.

In at least one embodiment, it may be determined that there is contact between body tissue surrounding test point 202 and probe hood 108 when contact sensor 122 is in contact with the body tissue of test subject 200. Contact sensor 122 may be configured to determine contact with body tissue or other objects, and/or may be configured to determine a force level experienced by the probe hood 108 by detecting a level of force exerted against contact sensor 122.

Sufficiently accurate readings are possible as long as probe tip 106 is on the correct desired test location and at the correct angle, and probe hood 108 maintains or remains in constant sufficient contact with the tissue surrounding test point 202. Verifying that probe hood 108 of electrodermal probe 110 remains in contact with body tissues surrounding test point 202 would validate that the bioelectric conductance test on the designated point is not compromised. There can be many embodiments to ensure that probe hood 108 remains in contact with the body tissues surrounding test point 202. Additionally, contact sensor 122 may have different functions in different embodiments to ensure that probe hood 108 remains in contact with the body tissue being tested/measured.

For example, in at least one embodiment, contact sensor 122 may be, and/or utilize, one or more contact switches located between probe hood 108 and the body tissue of test subject 200. A state in which a contact switch is in contact with body tissue of test subject 200 may be referred to as a contact state of contact switch or contact sensor 122. A state in which a contact switch is not in contact with body tissue of test subject 200 may be referred to as a non-contact state of contact switch or contact sensor 122. Contact sensor 122, acting as a contact switch, may operate such that it may be determined that probe hood 108 is in contact with body tissue of test subject 200 if contact sensor 122 is triggered to the contact state by being pressed against body tissue of test subject 200 to sufficiently register that contact sensor 122 is in contact with the body tissue. If probe hood 108 becomes separated from the body tissue of test subject 200, then contact sensor 122, acting as a contact switch, would be released to the non-contact state, which would indicate that probe hood 108 is not in contact with test subject 200.

The processor and computer program stored in bioelectric measurement analyzing device 118 may then register the release of the contact switch or contact sensor 122 to the non-contact state and, as a result, determine that probe hood 108 is not in contact with the body tissue of test subject 200. As a result of said determination, bioelectric measurement analyzing device 118 may then activate an alert to make the practitioner aware that contact between probe hood 108 and the body tissue of test subject 200 has been lost. Bioelectric measurement analyzing device 118 may then initiate a process to invalidate the reading being taken at the time when contact was lost. The alert to the practitioner may be an audio, visual, or tactile alert.

FIG. 5 illustrates steps of a method 500 for validating contact between probe hood 108 and body tissue. In step 502, it is determined, based on a reading from contact sensor 122, that probe hood 108 is in contact with the body tissue of test subject 200. In step 504, biometric and/or bioelectric measurements for test subject 200 are taken by electrodermal probe 110. In step 506, it is determined, based on a reading from contact sensor 122, whether contact between probe hood 108 and body tissue of test subject 200 is broken or not. This is determined based on whether the contact switch of contact sensor 122 is in the contact state or non-contact state. In step 508, when it is determined that contact between probe hood 108 and body tissue of test subject 200 is broken, an alert is output from bioelectric measurement analyzing device 118. The alert may be audio, visual, or tactile. Finally, in step 510, a bioelectric or biometric measurement being taken when the contact between probe hood 108 and body tissue of test subject 200 is broken is invalidated.

Figure 6:
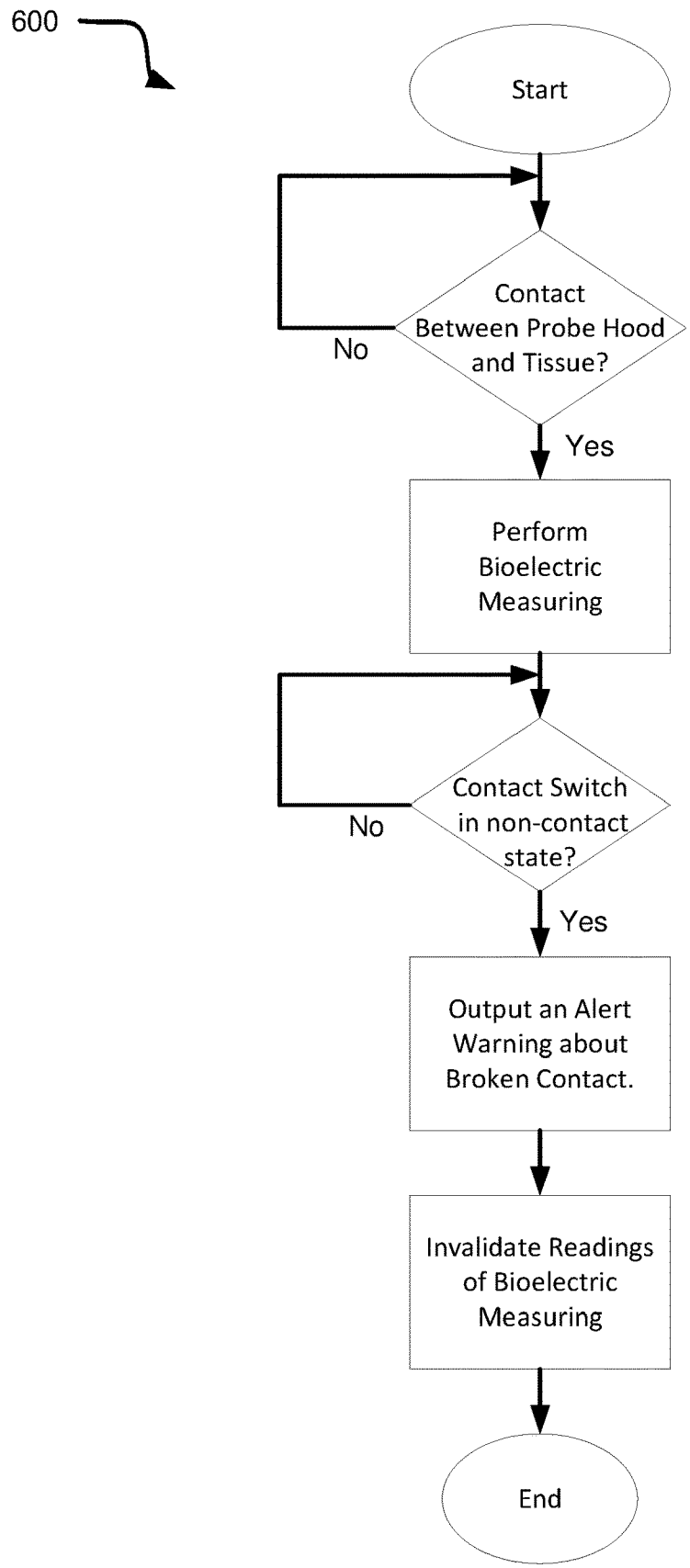
FIG. 6 illustrates a processing flow chart diagram of instructions executable by a computer for validating contact between an electrodermal probe and a test subject using a contact switch.

FIG. 6 illustrates a processing flow chart diagram of instructions 600 executable by a computer for validating contact between an electrodermal probe and a test subject using a contact switch for contact sensor 122. FIG. 6 illustrates the processing steps for method 500 shown in FIG. 5. For example, FIG. 6 illustrates that the processing begins at the Start point. After processing begins, the processing determines whether or not there is contact between probe hood 108 and body tissue, based on whether the state of contact sensor 122 indicates contact or non-contact (e.g., contact sensor 122, acting as a contact switch, is in a contact state or a non-contact state). If there is no contact (e.g., contact sensor 122 indicates no contact), then the process continually checks for contact between probe hood 108 and body tissue. On the other hand, if there is contact (e.g., contact sensor 122 indicates contact), then the processing proceeds to a step where electrodermal probe performs bioelectric measuring on the test subject.

During the bioelectric measuring, the state of contact sensor 122 is checked continually to determine whether or not contact between probe hood 108 and body tissue is broken (e.g., contact sensor 122 goes from contact state to non-contact state). If contact is maintained (e.g., contact sensor 122 stays in the contact state), then the process continues to check the state of contact sensor 122. If contact is broken (e.g., contact sensor 122 goes from contact state to non-contact state), then the process proceeds to output an alert warning about the broken contact and initiates a process to invalidate readings of bioelectric measuring that were compromised when contact was broken. The process may then conclude.

In another embodiment, contact sensor 122 may be, and/or utilize, one or more electrically conductive contacts on probe hood 108 that create a circuit between grounding device 102 held in one hand and the electrically conductive contacts on probe hood 108 that would be touching the skin or body tissue surrounding test point 202 on test subject 200. Such a configuration would create a closed circuit between grounding device 102 and the electrically conductive contacts on probe hood 108 when test subject 200 is holding grounding device 102 and the electrically conductive contacts of contact sensor 122 are in contact with the skin or body tissue of test subject 200.

Such a configuration could be used to monitor probe hood 108 contact on the body tissue of test subject 200. For example, if at any point during the test sequence probe hood 108 separates from the skin or body tissue surrounding test point 202, the circuit would be broken, which break may be used to indicate that probe hood 108 is no longer in contact with the body tissue of test subject 200.

The processor and computer program stored in bioelectric measurement analyzing device 118 may then register the break of the closed circuit of contact sensor 122 between grounding device 102 and the electrically conductive contacts on probe hood 108 and, as a result, determine that probe hood 108 is not in contact with the body tissue of test subject 200. As a result of said determination, bioelectric measurement analyzing device 118 may then activate an alert to make the practitioner aware that contact between probe hood 108 and body tissue of test subject 200 has been lost. Bioelectric measurement analyzing device 118 may then initiate a process to invalidate the reading being taken at the time when contact was lost. The alert to the practitioner may be an audio, visual, or tactile alert.

Furthermore, an advantage of utilizing electrically conductive contacts as contact sensor 122 would be that, with the body tissue being part of the circuit, you could measure and monitor the resistance of the skin. The harder a practitioner pushes against body tissue with electrodermal probe 110, the more conductivity the practitioner would be able to measure. So, in addition to knowing when the circuit is broken from separation between body tissue and probe hood 108, bioelectric measurement analyzing device 118 may also determine how hard probe hood 108 is pressed against the skin from the resistance measurement and predict or warn a practitioner about the lessening the force between body tissue and probe hood 108 before separation between body tissue and probe hood 108 occurs.

The steps illustrated in FIG. 5 showing method 500 for validating contact between probe hood 108 and body tissue, also apply to a situation where electrically conductive contacts are used. For example, in step 502, it is determined, based on a reading from contact sensor 122, that probe hood 108 is in contact with the body tissue of test subject 200. This contact is a result of closing the circuit formed with electrically conductive contacts of contact sensor 122. In step 504, biometric and/or bioelectric measurements for test subject 200 are taken by electrodermal probe 110. In step 506, it is determined, based on a reading from contact sensor 122, whether contact between probe hood 108 and body tissue of test subject 200 is broken or not. This is determined based on whether the closed circuit of contact sensor 122 is broken or conducting. In step 508, when it is determined that contact between probe hood 108 and body tissue of test subject 200 is broken, an alert is output from bioelectric measurement analyzing device 118. The alert may be audio, visual, or tactile. Finally, in step 510, a bioelectric or biometric measurement being taken when the contact between probe hood 108 and body tissue of test subject 200 is broken is invalidated.

Figure 7:
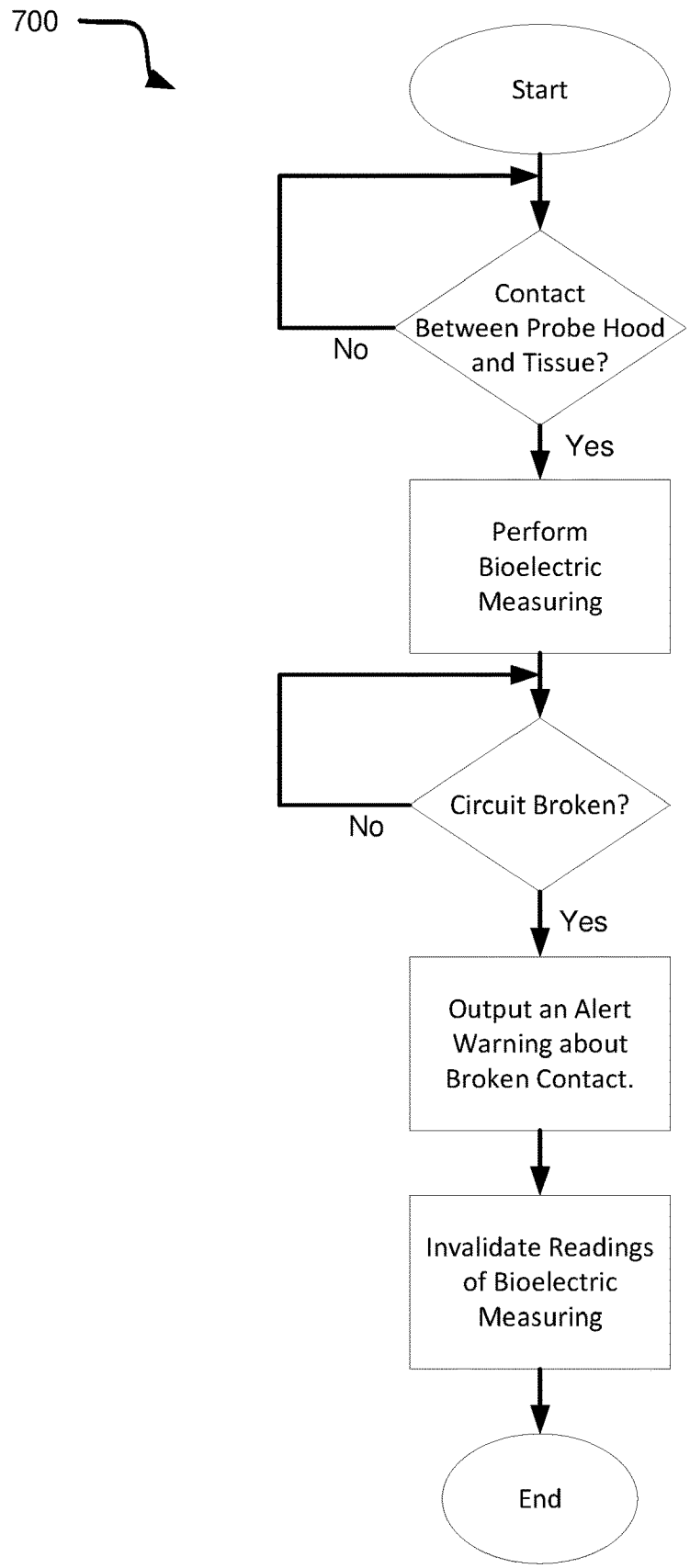
FIG. 7 illustrates a processing flow chart diagram of instructions executable by a computer for validating contact between an electrodermal probe and a test subject using electrically conductive contacts.

FIG. 7 illustrates a processing flow chart diagram of instructions 700 executable by a computer for validating contact between an electrodermal probe and a test subject using an electrically conductive contacts for contact sensor 122. For example, FIG. 7 illustrates that the processing begins at the start point. After processing begins, the processing determines whether or not there is contact between probe hood 108 and body tissue, based on whether the state of contact sensor 122 indicates contact or non-contact (e.g., electrically conductive contacts of contact sensor 122 form a closed circuit or do not form a closed circuit). If there is no contact (e.g., electrically conductive contacts of contact sensor 122 do not create a closed circuit), then the process continually checks for contact between probe hood 108 and body tissue. On the other hand, if there is contact (e.g., electrically conductive contacts of contact sensor 122 form closed circuit), then the processing proceeds to a step where electrodermal probe performs bioelectric measuring on the test subject.

During the bioelectric measuring, the state of contact sensor 122 is checked continually to determine whether or not contact between probe hood 108 and body tissue is broken (e.g., electrically conductive contacts of contact sensor 122 go from conducting state to non-conducting state). If contact is maintained (e.g., electrically conductive contacts of contact sensor 122 remain in conducting state), then the process continues to check the state of contact sensor 122. If contact is broken (e.g., electrically conductive contacts of contact sensor 122 go from conducting state to non-conducting state), then the process proceeds to output an alert warning about the broken contact and initiates a process to invalidate readings of bioelectric measuring that were compromised when contact was broken. The process may then conclude.

In another embodiment, contact sensor 122 may be, and/or utilize, one or more force sensors, such as a tip force sensor and a hood force sensor, that monitor one or both of the force applied at probe hood 108 and the force applied at the probe tip 106. With forces applied at probe hood 108 and at the probe tip 106 being monitored, it is possible to compare the probe hood force to the probe tip force.

Force levels of the probe hood force and the probe tip force may be used to determine, verify, and maintain contact between probe tip 106 and body tissue, and between probe hood 108 and body tissue. For example, as long as the force on probe hood 108 is greater than or equal to the force on probe tip 106 during the test sequence then the computerized system can control the motor so that the motor is the only influence applying force on probe tip 106 against test point 202 of test subject 200. If the force on probe hood 108 becomes less than the force on probe tip 106, then the probe hood 108 will separate from the skin or body tissue surrounding test point 202. As a result, other outside influences and/or forces besides the motor can influence the test sequence and readings and can compromise the results.

The processor and computer program stored in bioelectric measurement analyzing device 118 may then register that the force on probe hood 108 becomes less than the force on probe tip 106 of electrodermal probe 110. As a result, bioelectric measurement analyzing device 118 may then activate an alert to make the practitioner aware that contact between probe hood 108 and the body tissue of test subject 200 may be lost. Bioelectric measurement analyzing device 118 may then initiate a process to invalidate the reading being taken at the time when force on probe hood 108 became less then force on probe tip 106. The alert to the practitioner may be an audio, visual, or tactile alert. There could be many other means devised to determine if a bioelectric electrodermal probe maintains continual contact with tissue during a test sequence.

FIG. 8 illustrates steps of a method 800 for validating contact between probe hood 108 and body tissue. In step 802, it is determined, based on a reading from contact sensor 122, that probe hood 108 is in contact with the body tissue of test subject 200. In step 804, biometric and/or bioelectric measurements for test subject 200 are taken by electrodermal probe 110. In step 806, a tip force on probe tip 106, based on a reading from a tip sensor, is compared to a hood force on probe hood 108, based on a reading of a hood sensor, to determine whether contact between probe hood 108 and body tissue of test subject 200 is broken or not. In step 808, it is determined that contact is broken between probe hood 108 and body tissue of test subject 200 when the hood force is less than the tip force. In step 810, when it is determined that contact between probe hood 108 and body tissue of test subject 200 is broken, an alert is output from bioelectric measurement analyzing device 118. The alert may be audio, visual, or tactile. Finally, in step 812, a bioelectric or biometric measurement being taken when the contact between probe hood 108 and body tissue of test subject 200 is broken is invalidated.

Figure 9:
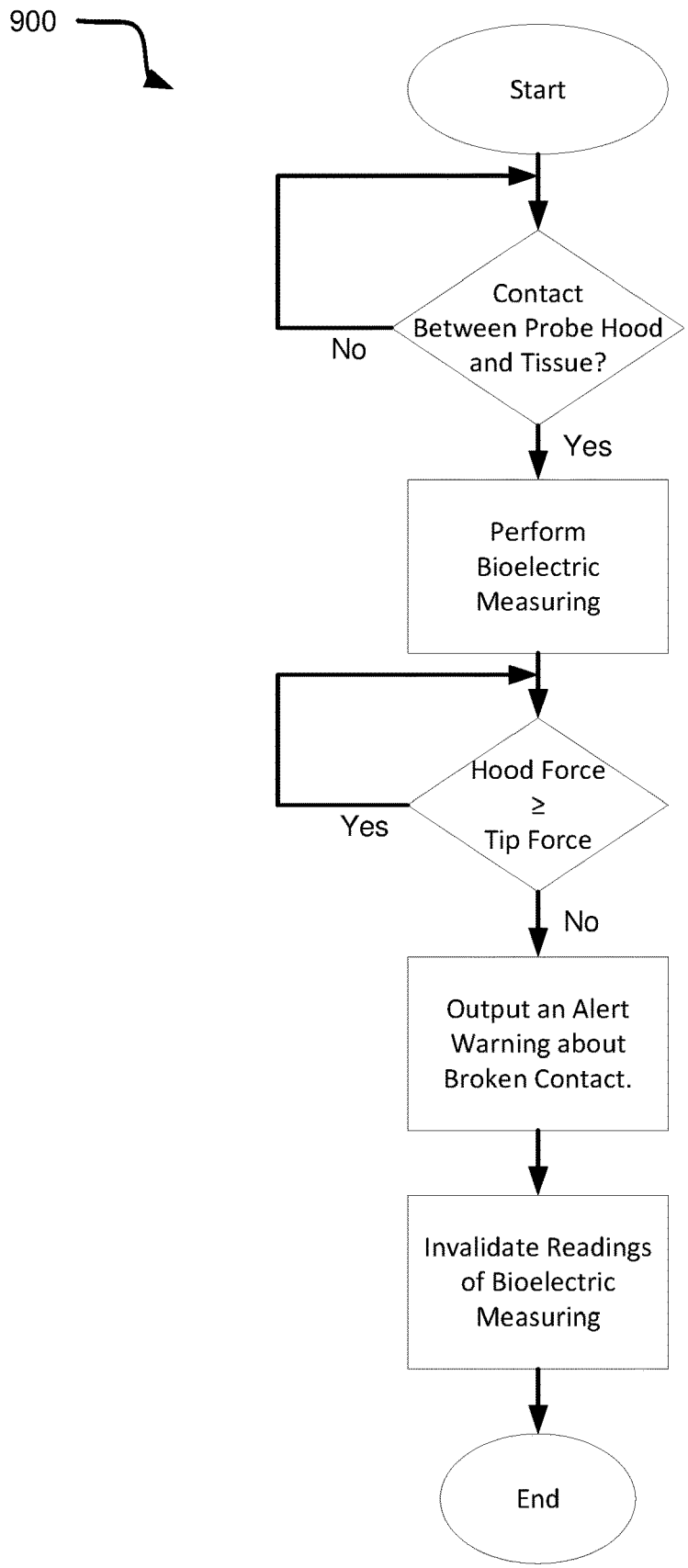
FIG. 9 illustrates a processing flow chart diagram of instructions executable by a computer for validating contact between an electrodermal probe and a test subject using force sensors.

FIG. 9 illustrates a processing flow chart diagram of instructions 900 executable by a computer for validating contact between an electrodermal probe and a test subject using force sensors for contact sensor 122. FIG. 9 illustrates the processing steps for method 800 shown in FIG. 8. For example, FIG. 8 illustrates that the processing begins at the start point. After processing begins, the processing determines whether or not there is contact between probe hood 108 and body tissue, based on whether the state of contact sensor 122 indicates contact or non-contact (e.g., force sensors of contact sensor 122 indicate that hood force is greater than or equal to tip force). If there is no contact (e.g., hood force less than tip force), then the process continually checks for contact between probe hood 108 and body tissue. On the other hand, if there is contact (e.g., hood force greater than or equal to tip force), then the processing proceeds to a step where electrodermal probe performs bioelectric measuring on the test subject.

During the bioelectric measuring, the state of contact sensor 122 is checked continually to determine whether or not contact between probe hood 108 and body tissue is broken (e.g., hood force becomes less than tip force). If contact is maintained (e.g., hood force is greater than or equal to tip force), then the process continues to check the state of contact sensor 122. If contact is broken (e.g., hood force is less than tip force), then the process proceeds to output an alert warning about the broken contact and initiates a process to invalidate readings of bioelectric measuring that were compromised when contact was broken. The process may then conclude.

Other embodiments are possible. For example, one force sensor may be used to determine if there is contact between electrodermal probe 110 and body tissue as long as the force on the one force sensor registers force above a threshold value. Such a force sensor may be on probe hood 108 or probe tip 106. In such a case, comparing hood force and tip force may be unnecessary.

Advantages of the above-described embodiments are that technicians and practitioners using such devices will be better able to obtain reliable and accurate readings, even with little experience, by being alerted to problems such as contact between test probes and test subjects being broken during testing. Additionally, erroneous or inaccurate readings may be invalidated or deleted, leading to more accurate measuring and analysis on bioelectric measurements.

Figure 10:
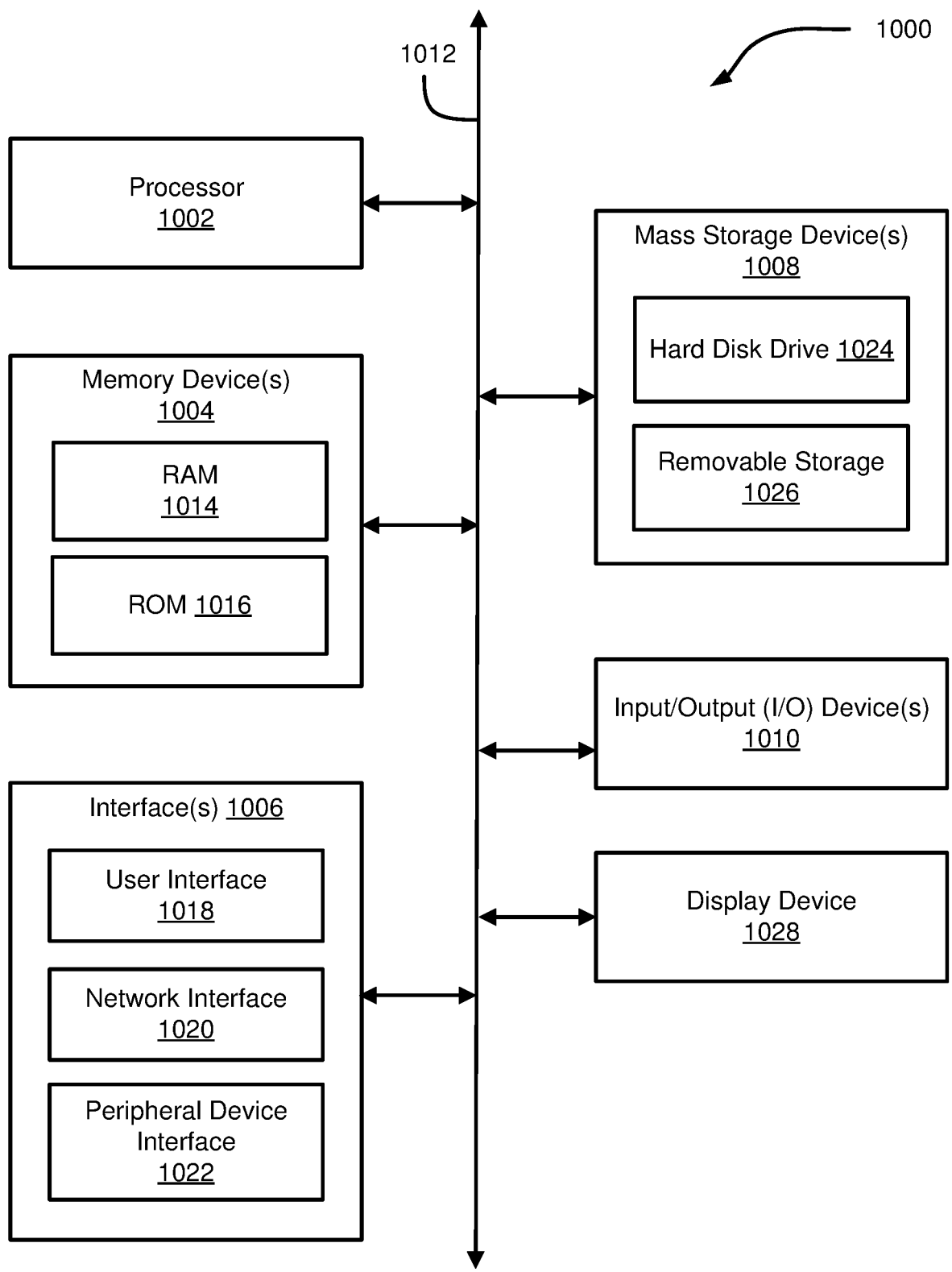
FIG. 10 is a block diagram of an example computing device in accordance with the teachings and principles of the disclosure.

FIG. 10 is a block diagram illustrating an example computing device 1000. Computing device 1000 may be used to perform various procedures, such as those discussed herein. Computing device 1000 can function as a server, a client, or any other computing entity such as one or more processors of bioelectric measurement analyzing device 118 in communication with the electrodermal probe 110 and/or the grounding device 102. Computing device can perform various monitoring functions as discussed herein, and can execute one or more application programs, such as the application programs described herein. Computing device 1000 can be any of a wide variety of computing devices, such as a desktop computer, a notebook computer, a server computer, a handheld computer, tablet computer and the like.

Computing device 1000 may include one or more processor(s) 1002, one or more memory device(s) 1004, one or more interface(s) 1006, one or more mass storage device(s) 1008, one or more Input/Output (I/O) device(s) 1010, and a display device 1028 all of which are coupled to a bus 1012. Processor(s) 1002 include one or more processors or controllers that execute instructions stored in memory device(s) 1004 and/or mass storage device(s) 1008. Processor(s) 1002 may also include various types of computer-readable media, such as cache memory.

Memory device(s) 1004 include various computer-readable media, such as volatile memory (e.g., random access memory (RAM) 1014) and/or nonvolatile memory (e.g., read-only memory (ROM) 1016). Memory device(s) 1004 may also include rewritable ROM, such as Flash memory.

Mass storage device(s) 1008 include various computer readable media, such as magnetic tapes, magnetic disks, optical disks, solid-state memory (e.g., Flash memory), and so forth. As shown in FIG. 10, a particular mass storage device is a hard disk drive 1024. Various drives may also be included in mass storage device(s) 1008 to enable measurement from and/or writing to the various computer readable media. Mass storage device(s) 1008 include removable storage 1026 and/or non-removable media.

I/O device(s) 1010 include various devices that allow data and/or other information to be input to or retrieved from computing device 1000. Example I/O device(s) 1010 include cursor control devices, keyboards, keypads, microphones, monitors or other display devices, speakers, printers, network interface cards, modems, lenses, CCDs or other image capture devices, and the like.

Display device 1028 includes any type of device capable of displaying information to one or more users of computing device 1000. Examples of display device 1028 include a monitor, display terminal, video projection device, and the like.

Interface(s) 1006 include various interfaces that allow computing device 1000 to interact with other systems, devices, or computing environments. Example interface(s) 1006 may include any number of different network interfaces 1020, such as interfaces to local area networks (LANs), wide area networks (WANs), wireless networks, and the Internet. Other interface(s) include user interface 1018 and peripheral device interface 1022. The interface(s) 1006 may also include one or more user interface elements 1018. The interface(s) 1006 may also include one or more peripheral interfaces such as interfaces for printers, pointing devices (mice, track pad, or any suitable user interface now known to those of ordinary skill in the field, or later discovered), keyboards, and the like.

Bus 1012 allows processor(s) 1002, memory device(s) 1004, interface(s) 1006, mass storage device(s) 1008, and I/O device(s) 1010 to communicate with one another, as well as other devices or components coupled to bus 1012. Bus 1012 represents one or more of several types of bus structures, such as a system bus, PCI bus, IEEE 1394 bus, USB bus, and so forth.

For purposes of illustration, programs and other executable program components are shown herein as discrete blocks, although it is understood that such programs and components may reside at various times in different storage components of computing device 1000, and are executed by processor(s) 1002. Alternatively, the systems and procedures described herein can be implemented in hardware, or a combination of hardware, software, and/or firmware. For example, one or more application specific integrated circuits (ASICs) can be programmed to carry out one or more of the systems and procedures described herein.

Implementations of the disclosure may comprise or utilize a special purpose or general-purpose computer including computer hardware, such as, for example, one or more processors and system memory, as discussed in greater detail below. Implementations within the scope of the disclosure also include physical and other computer-readable media for carrying or storing computer-executable instructions and/or data structures. Such computer-readable media can be any available media that can be accessed by a general purpose or special purpose computer system. Computer-readable media that store computer-executable instructions are computer storage media (devices). Computer-readable media that carry computer-executable instructions are transmission media. Thus, by way of example, and not limitation, implementations of the disclosure can comprise at least two distinctly different kinds of computer-readable media: computer storage media (devices) and transmission media.

Computer storage media (devices) includes RAM, ROM, EEPROM, CD-ROM, solid state drives ("SSDs") (e.g., based on RAM), Flash memory, phase-change memory ("PCM"), other types of memory, other optical disk storage, magnetic disk storage or other magnetic storage devices, or any other medium which can be used to store desired program code means in the form of computer-executable instructions or data structures and which can be accessed by a general purpose or special purpose computer.

A "network" is defined as one or more data links that enable the transport of electronic data between computer systems and/or modules and/or other electronic devices. When information is transferred or provided over a network or another communications connection (either hardwired, wireless, or a combination of hardwired or wireless) to a computer, the computer properly views the connection as a transmission medium. Transmission media can include a network and/or data links, which can be used to carry desired program code means in the form of computer-executable instructions or data structures and which can be accessed by a general purpose or special purpose computer. Combinations of the above should also be included within the scope of computer-readable media.

Further, upon reaching various computer system components, program code means in the form of computer-executable instructions or data structures can be transferred automatically from transmission media to computer storage media devices or vice versa. For example, computer-executable instructions or data structures received over a network or data link can be buffered in RAM 1014 within a network interface module 1020 (e.g., a "NIC"), and then eventually transferred to computer system RAM 1014 and/or to less volatile computer storage media (devices) at a computer system. RAM 1014 can also include solid state drives (SSDs or PCIx based real time memory tiered storage, such as FusionIO). Thus, it should be understood that computer storage media devices can be included in computer system components that also (or even primarily) utilize transmission media.

Computer-executable instructions comprise, for example, instructions and data which, when executed at a processor, cause a general purpose computer, special purpose computer, or special purpose processing device to perform a certain function or group of functions. The computer executable instructions may be, for example, binaries, intermediate format instructions such as assembly language, or even source code. Although the subject matter has been described in language specific to structural features and/or methodological acts, it is to be understood that the subject matter defined in the appended claims is not necessarily limited to the described features or acts described above. Rather, the described features and acts are disclosed as example forms of implementing the claims.

Those skilled in the art will appreciate that the disclosure may be practiced in network computing environments with many types of computer system configurations, including personal computers, desktop computers, laptop computers, message processors, hand-held devices, multi-processor systems, microprocessor-based or programmable consumer electronics, network PCs, minicomputers, mainframe computers, mobile telephones, PDAs, tablets, pagers, routers, switches, various storage devices, and the like. The disclosure may also be practiced in distributed system environments where local and remote computer systems, which are linked (either by hardwired data links, wireless data links, or by a combination of hardwired and wireless data links) through a network, both perform tasks. In a distributed system environment, program modules may be located in both local and remote memory storage devices.

Implementations of the disclosure can also be used in cloud computing environments. In this description and the following claims, "cloud computing" is defined as a model for enabling ubiquitous, convenient, on-demand network access to a shared pool of configurable computing resources (e.g., networks, servers, storage, applications, and services) that can be rapidly provisioned via virtualization and released with minimal management effort or service provider interaction, and then scaled accordingly. A cloud model can be composed of various characteristics (e.g., on-demand self-service, broad network access, resource pooling, rapid elasticity, measured service, or any suitable characteristic now known to those of ordinary skill in the field, or later discovered), service models (e.g., Software as a Service (SaaS), Platform as a Service (PaaS), Infrastructure as a Service (IaaS)), and deployment models (e.g., private cloud, community cloud, public cloud, hybrid cloud, or any suitable service type model now known to those of ordinary skill in the field, or later discovered). Databases and servers described with respect to the disclosure can be included in a cloud model.

Further, where appropriate, functions described herein can be performed in one or more of: hardware, software, firmware, digital components, or analog components. For example, one or more application specific integrated circuits (ASICs) can be programmed to carry out one or more of the systems and procedures described herein. Certain terms are used throughout the following description and Claims to refer to particular system components. As one skilled in the art will appreciate, components may be referred to by different names. This document does not intend to distinguish between components that differ in name, but not function.

The disclosure applies to all embodiments, methods, systems, devices, and computer program products that could be utilized to validate continual probe or probe hood contact with a test subject's tissue or tissue surrounding a test point. Included with skin or tissue contact validation; warnings, alerts, and systems and procedures that could invalidate a compromised reading and initiate a new reading at the compromised test point.

EXAMPLES

The following examples pertain to further embodiments.

Example 1 is a device including an electrodermal probe that takes biometric measurements of a test subject, including a probe tip disposed at the testing end of the electrodermal probe, a probe hood disposed to surround the probe tip, a contact sensor disposed on the probe hood that senses contact between the probe hood and body tissue of a test subject, and one or more processors in electrical communication with the electrodermal probe and configurable to execute instructions stored in non-transitory computer readable storage media. The instructions include determining, based on a reading from the contact sensor, that the probe hood is in contact with the body tissue of the test subject, receiving a biometric measurement for the test subject from the electrodermal probe, determining, based on the reading from the contact sensor, whether contact between the probe hood and the body tissue is broken; and outputting an alert in a case where it is determined that contact between the probe hood and the body tissue has been broken.

Example 2 is a device as in Example 1, wherein the contact sensor comprises a contact switch.

Example 3 is a device as in any of Examples 1 and 2, wherein the contact switch has a contact state and a non-contact state. It is determined that the probe hood is in contact with the body tissue of the test subject when the contact switch is in the contact state and it is determined that the probe hood is not in contact with the body tissue of the test subject when the contact switch is in the non-contact state.

Example 4 is a device as in any of Examples 1-3, wherein the contact sensor comprises one or more electrically conductive contacts.

Example 5 is a device as in any of Examples 1-4, wherein it is determined that the probe hood is in contact with the body tissue of the test subject when the one or more electrically conductive contacts are in contact with the body tissue and create a closed circuit between the body tissue and the one or more electrically conductive contacts of the contact sensor. It is determined that the probe hood is not in contact with the body tissue when the one or more electrically conductive contacts are not in contact with the body tissue and the closed circuit is broken.

Example 6 is a device as in any of Examples 1-5, wherein the contact sensor comprises one or more force sensors.

Example 7 is a device as in any of Examples 1-6, wherein the one or more sensors comprise a tip force sensor on the probe tip and a hood force sensor on the probe hood.

Example 8 is a device as in any of Examples 1-7, wherein the step of determining whether contact between the probe hood and the body tissue is broken includes comparing a tip force, based on a reading from the tip force sensor, to a hood force, based on a reading from the hood force sensor, and determining, in a case where the hood force is less than the tip force, that contact between the probe hood and the body tissue is broken.

Example 9 is a device as in any of Examples 1-8, wherein the instructions further comprise invalidating the biometric measurement received from the electrodermal probe in a case where it is determined that contact between the probe hood and the body tissue has been broken during the reading.

Example 10 is a method of operation for an electrodermal probe including a probe tip that takes biometric measurements of a test subject, a probe hood disposed to surround the probe tip, and a contact sensor disposed on the probe hood that senses contact between the probe hood and body tissue of a test subject. The method includes determining, based on a reading from the contact sensor, that the probe hood is in contact with the body tissue of the test subject, receiving a biometric measurement for the test subject from the electrodermal probe, determining, based on the reading from the contact sensor, whether contact between the probe hood and the body tissue is broken, and outputting an alert in a case where it is determined that contact between the probe hood and the body tissue has been broken.

Example 11 is a method as in Example 10, wherein the contact sensor comprises a contact switch having a contact state and a non-contact state. It is determined that the probe hood is in contact with the body tissue of the test subject when the contact switch is in the contact state and it is determined that the probe hood is not in contact with the body tissue of the test subject when the contact switch is in the non-contact state.

Example 12 is a method as in Examples 10 and 11, wherein the contact sensor comprises one or more electrically conductive contacts. It is determined that the probe hood is in contact with the body tissue of the test subject when the one or more electrically conductive contacts are in contact with the body tissue and create a closed circuit between the body tissue and the one or more electrically conductive contacts of the contact sensor. It is determined that the probe hood is not in contact with the body tissue when the one or more electrically conductive contacts are not in contact with the body tissue and the closed circuit is broken.

Example 13 is a method as in any of Examples 10-12, wherein the contact sensor comprises a tip force sensor on the probe tip and a hood force sensor on the probe hood. The step of determining whether contact between the probe hood and the body tissue is broken includes comparing a tip force, based on a reading from the tip force sensor, to a hood force, based on a reading from the hood force sensor, and determining, in a case where the hood force is less than the tip force, that contact between the probe hood and the body tissue is broken.

Example 14 is a method as in any of Examples 10-13, wherein the instructions further comprise invalidating the biometric measurement received from the electrodermal probe in a case where it is determined that contact between the probe hood and the body tissue has been broken during the reading.

Example 15 is non-transitory computer readable storage media storing instructions to be executed by one or more processors in an electrodermal probe including a probe tip that takes biometric measurements of a test subject, a probe hood disposed to surround the probe tip, and a contact sensor disposed on the probe hood that senses contact between the probe hood and body tissue of a test subject. The instructions include determining, based on a reading from the contact sensor, that the probe hood is in contact with the body tissue of the test subject, receiving a biometric measurement for the test subject from the electrodermal probe, determining, based on the reading from the contact sensor, whether contact between the probe hood and the body tissue is broken, and outputting an alert in a case where it is determined that contact between the probe hood and the body tissue has been broken.

Example 16 is non-transitory computer readable storage media as in Example 15, wherein the contact sensor comprises a contact switch having a contact state and a non-contact state. The instructions are such that it is determined that the probe hood is in contact with the body tissue of the test subject when the contact switch is in the contact state and it is determined that the probe hood is not in contact with the body tissue of the test subject when the contact switch is in the non-contact state.

Example 17 is non-transitory computer readable storage media as in Examples 15 and 16, wherein the contact sensor comprises one or more electrically conductive contacts. The instructions are such that it is determined that the probe hood is in contact with the body tissue of the test subject when the one or more electrically conductive contacts are in contact with the body tissue and create a closed circuit between the body tissue and the one or more electrically conductive contacts of the contact sensor and it is determined that the probe hood is not in contact with the body tissue when the one or more electrically conductive contacts are not in contact with the body tissue and the closed circuit is broken.

Example 18 is non-transitory computer readable storage media as in Example 15-17, wherein the contact sensor comprises a tip force sensor on the probe tip and a hood force sensor on the probe hood. The instructions are such that the step of determining whether contact between the probe hood and the body tissue is broken includes comparing a tip force, based on a reading from the tip force sensor, to a hood force, based on a reading from the hood force sensor, and determining, in a case where the hood force is less than the tip force, that contact between the probe hood and the body tissue is broken.

Example 19 is a method as in any of Examples 15-18, wherein the instructions further comprise invalidating the biometric measurement received from the electrodermal probe in a case where it is determined that contact between the probe hood and the body tissue has been broken during the reading.

The foregoing description has been presented for the purposes of illustration and description. It is not intended to be exhaustive or to limit the disclosure to the precise form disclosed. Many modifications and variations are possible in light of the above teaching. Further, it should be noted that any or all of the aforementioned alternate implementations and embodiments may be used in any combination desired to form additional hybrid implementations and embodiments of the disclosure.

Further, although specific implementations of the disclosure have been described and illustrated, the disclosure is not to be limited to the specific forms or arrangements of parts so described and illustrated. The scope of the disclosure is to be defined by the claims appended hereto, any future claims submitted here and in different applications, and their equivalents.

What is claimed is:

1. A device comprising:
   an electrodermal probe that takes a biometric measurement of a test subject, the biometric measurement comprising one or more of resistance and conductance of body tissue located under a skin of the test subject, the electrodermal probe comprising:
   a probe tip disposed at a testing end of the electrodermal probe;
   a probe hood disposed to surround the probe tip; and
   a contact sensor disposed on an outer surface of the probe hood, such that the contact sensor is positioned to contact the body tissue of the test subject during the biometric measurement, wherein the contact sensor senses contact between the probe hood and the body tissue of the test subject; and
   one or more processors in electrical communication with the electrodermal probe and configurable to execute instructions stored in non-transitory computer readable storage media, the instructions comprising:
   determining, based on a reading from the contact sensor, that the probe hood is in contact with the body tissue of the test subject;
   receiving the biometric measurement for the test subject from the electrodermal probe;
   determining, based on the reading from the contact sensor, whether contact between the probe hood and the body tissue is broken; and
   outputting an alert in a case where it is determined that contact between the probe hood and the body tissue has been broken.

2. The device of claim 1, wherein the contact sensor comprises a contact switch.

3. The device of claim 2, wherein the contact switch has a contact state and a non-contact state; and
   wherein it is determined that the probe hood is in contact with the body tissue of the test subject when the contact switch is in the contact state and it is determined that the probe hood is not in contact with the body tissue of the test subject when the contact switch is in the non-contact state.

4. The device of claim 1, wherein the contact sensor comprises one or more electrically conductive contacts.

5. The device of claim 4, wherein it is determined that the probe hood is in contact with the body tissue of the test subject when the one or more electrically conductive contacts are in contact with the body tissue and create a closed circuit between the body tissue and the one or more electrically conductive contacts of the contact sensor and it is determined that the probe hood is not in contact with the body tissue when the one or more electrically conductive contacts are not in contact with the body tissue and the closed circuit is broken.

6. The device of claim 1, wherein the contact sensor comprises one or more force sensors.

7. The device of claim 6, wherein the one or more sensors comprise a tip force sensor on the probe tip and a hood force sensor on the probe hood.

8. The device of claim 7, wherein the step of determining whether contact between the probe hood and the body tissue is broken comprises:
    comparing a tip force, based on a reading from the tip force sensor, to a hood force, based on a reading from the hood force sensor;
    determining, in a case where the hood force is less than the tip force, that contact between the probe hood and the body tissue is broken.

9. The device of claim 1, wherein the instructions further comprise invalidating the biometric measurement received from the electrodermal probe in a case where it is determined that contact between the probe hood and the body tissue has been broken during the reading.

10. The device of claim 1,
    wherein the device is an Electroacupuncture According to Voll (EAV) device;
    wherein the electrodermal probe takes the biometric measurement of the test subject, the biometric measurement comprising one or more of:
    conductance of meridian points within the test subject;
    resistance of a meridian pathway within the test subject.

11. A method of operation for an electrodermal probe that takes a biometric measurement of a test subject, the biometric measurement comprising one or more of resistance and conductance of body tissue located under a skin of the test subject, the electrodermal probe including a probe tip disposed at a testing end of the electrodermal probe, a probe hood disposed to surround the probe tip, and a contact sensor disposed on an outer surface of the probe hood, such that the contact sensor is positioned to contact the body tissue of the test subject during the biometric measurement, wherein the contact sensor senses contact between the probe hood and the body tissue of the test subject, the method comprising:
    determining, based on a reading from the contact sensor, that the probe hood is in contact with the body tissue of the test subject;
    receiving the biometric measurement for the test subject from the electrodermal probe;
    determining, based on the reading from the contact sensor, whether contact between the probe hood and the body tissue is broken; and
    outputting an alert in a case where it is determined that contact between the probe hood and the body tissue has been broken.

12. The method of claim 11, wherein the contact sensor comprises a contact switch having a contact state and a non-contact state; and
    wherein it is determined that the probe hood is in contact with the body tissue of the test subject when the contact switch is in the contact state and it is determined that the probe hood is not in contact with the body tissue of the test subject when the contact switch is in the non-contact state.

13. The method of claim 11, wherein the contact sensor comprises one or more electrically conductive contacts; and
    wherein it is determined that the probe hood is in contact with the body tissue of the test subject when the one or more electrically conductive contacts are in contact with the body tissue and create a closed circuit between the body tissue and the one or more electrically conductive contacts of the contact sensor and it is determined that the probe hood is not in contact with the body tissue when the one or more electrically conductive contacts are not in contact with the body tissue and the closed circuit is broken.

14. The method of claim 11, wherein the contact sensor comprises a tip force sensor on the probe tip and a hood force sensor on the probe hood; and
    wherein the step of determining whether contact between the probe hood and the body tissue is broken comprises:
        comparing a tip force, based on a reading from the tip force sensor, to a hood force, based on a reading from the hood force sensor; and
        determining, in a case where the hood force is less than the tip force, that contact between the probe hood and the body tissue is broken.

15. The method of claim 11, wherein the method further comprises invalidating the biometric measurement received from the electrodermal probe in a case where it is determined that contact between the probe hood and the body tissue has been broken during the reading.

16. Non-transitory computer readable storage media storing instructions to be executed by one or more processors of an electrodermal probe that takes a biometric measurement of a test subject, the biometric measurement comprising one or more of resistance and conductance of body tissue located under a skin of the test subject, the electrodermal probe including a probe tip disposed at a testing end of the electrodermal probe, a probe hood disposed to surround the probe tip, and a contact sensor disposed on an outer surface of the probe hood, such that the contact sensor is positioned to contact the body tissue of the test subject during the biometric measurement, wherein the contact sensor senses contact between the probe hood and the body tissue of the test subject, the instructions comprising:
    determining, based on a reading from the contact sensor, that the probe hood is in contact with the body tissue of the test subject;
    receiving the biometric measurement for the test subject from the electrodermal probe;
    determining, based on the reading from the contact sensor, whether contact between the probe hood and the body tissue is broken; and
    outputting an alert in a case where it is determined that contact between the probe hood and the body tissue has been broken.

17. The non-transitory computer readable storage media of claim 16, wherein the contact sensor comprises a contact switch having a contact state and a non-contact state; and
    wherein the instructions determine that the probe hood is in contact with the body tissue of the test subject when the contact switch is in the contact state and determine that the probe hood is not in contact with the body tissue of the test subject when the contact switch is in the non-contact state.

18. The non-transitory computer readable storage media of claim 16, wherein the contact sensor comprises one or more electrically conductive contacts; and wherein the instructions determine that the probe hood is in contact with the body tissue of the test subject when the one or more electrically conductive contacts are in contact with the body tissue and create a closed circuit between the body tissue and the one or more electrically conductive contacts of the contact sensor and the instructions determine that the probe hood is not in contact with the body tissue when the one or more electrically conductive contacts are not in contact with the body tissue and the closed circuit is broken.

19. The non-transitory computer readable storage media of claim 16, wherein the contact sensor comprises a tip force sensor on the probe tip and a hood force sensor on the probe hood; and wherein, in the instructions, the step of determining whether contact between the probe hood and the body tissue is broken comprises:

comparing a tip force, based on a reading from the tip force sensor, to a hood force, based on a reading from the hood force sensor; and determining, in a case where the hood force is less than the tip force, that contact between the probe hood and the body tissue is broken.

20. The non-transitory computer readable storage media of claim 16, wherein the instructions further comprise invalidating the biometric measurement received from the electrodermal probe in a case where it is determined that contact between the probe hood and the body tissue has been broken during the reading.

* * * * *